(12) United States Patent
Weigl et al.

(10) Patent No.: US 6,409,832 B2
(45) Date of Patent: Jun. 25, 2002

(54) PROTEIN CRYSTALLIZATION IN MICROFLUIDIC STRUCTURES

(75) Inventors: Bernhard H. Weigl, Seattle, WA (US); Jurgen Sygusch, Montréal (CA)

(73) Assignee: Micronics, Inc., Redmond, WA (US)

( * ) Notice: Subject to any disclaimer, the term of this patent is extended or adjusted under 35 U.S.C. 154(b) by 0 days.

(21) Appl. No.: 09/822,595

(22) Filed: Mar. 30, 2001

Related U.S. Application Data

(60) Provisional application No. 60/193,867, filed on Mar. 31, 2000.

(51) Int. Cl.[7] .............................................. C30B 35/00
(52) U.S. Cl. ........................ 117/206; 117/200; 117/900; 422/245.1
(58) Field of Search ................................ 117/200, 206, 117/900; 422/245.1

(56) References Cited

U.S. PATENT DOCUMENTS

| | | | |
|---|---|---|---|
| 5,716,852 A | * 2/1998 | Yager et al. | 436/172 |
| 5,726,404 A | * 3/1998 | Brody | 200/81 R |
| 5,922,210 A | * 7/1999 | Brody et al. | 210/767 |
| 5,932,100 A | * 8/1999 | Yager et al. | 210/634 |
| 5,948,684 A | * 9/1999 | Weigl et al. | 436/52 |
| 5,971,158 A | * 10/1999 | Yager et al. | 209/155 |
| 5,974,867 A | * 11/1999 | Forster et al. | 73/61.41 |
| 6,007,775 A | * 12/1999 | Yager | 422/57 |
| 6,258,331 B1 | 7/2001 | Sanjoh | |

FOREIGN PATENT DOCUMENTS

| | | |
|---|---|---|
| EP | 0815940 A | 1/1998 |
| WO | WO9923284 A | 5/1999 |

OTHER PUBLICATIONS

Sanjoh, Spatiotemporal Protein Crystal Growth Studies using Microfluidic Silicon Devices, Journal of Crystal Growth, Jan. 15, 1999, pp. 691–702 vol. 196, No. 2–4 North Holland Pub. Co. Amsterdam, NL.

Luft, Microbatch macromolecular crystallization in micropyettes Structure, Function and Growth, Journal of Crystal Growth, Jan. 15, 1999, pp. 447–449, vol. 196, No. 196, No. 2–4, North Holland Pub. Co., Amsterdam, NL.

Luft, Microbatch macromolecular crystallization on a thermal gradient, Journal of Crystal Growth, Jan. 15, 1999, vol. 196, No. 2–4, North Holland Pub. Co., Amsterdam, NL.

Fujitsu, Patent Abstracts of Japah, Method for Growing and Recovering Crystal, Pub. No. 3050177, Apr. 03, 1991, App. No. 01184155, Jul. 15, 1989.

* cited by examiner

*Primary Examiner*—Felisa Hiteshew
(74) *Attorney, Agent, or Firm*—Jerrold J. Litzinger

(57) ABSTRACT

A device for promoting protein crystal growth (PCG) using microfluidic channels. A protein sample and a solvent solution are combined within a microfluidic channel having laminar flow characteristics which forms diffusion zones, providing for a well defined crystallization. Protein crystals can then be harvested from the device. The device is particularly suited for microgravity conditions.

17 Claims, 5 Drawing Sheets

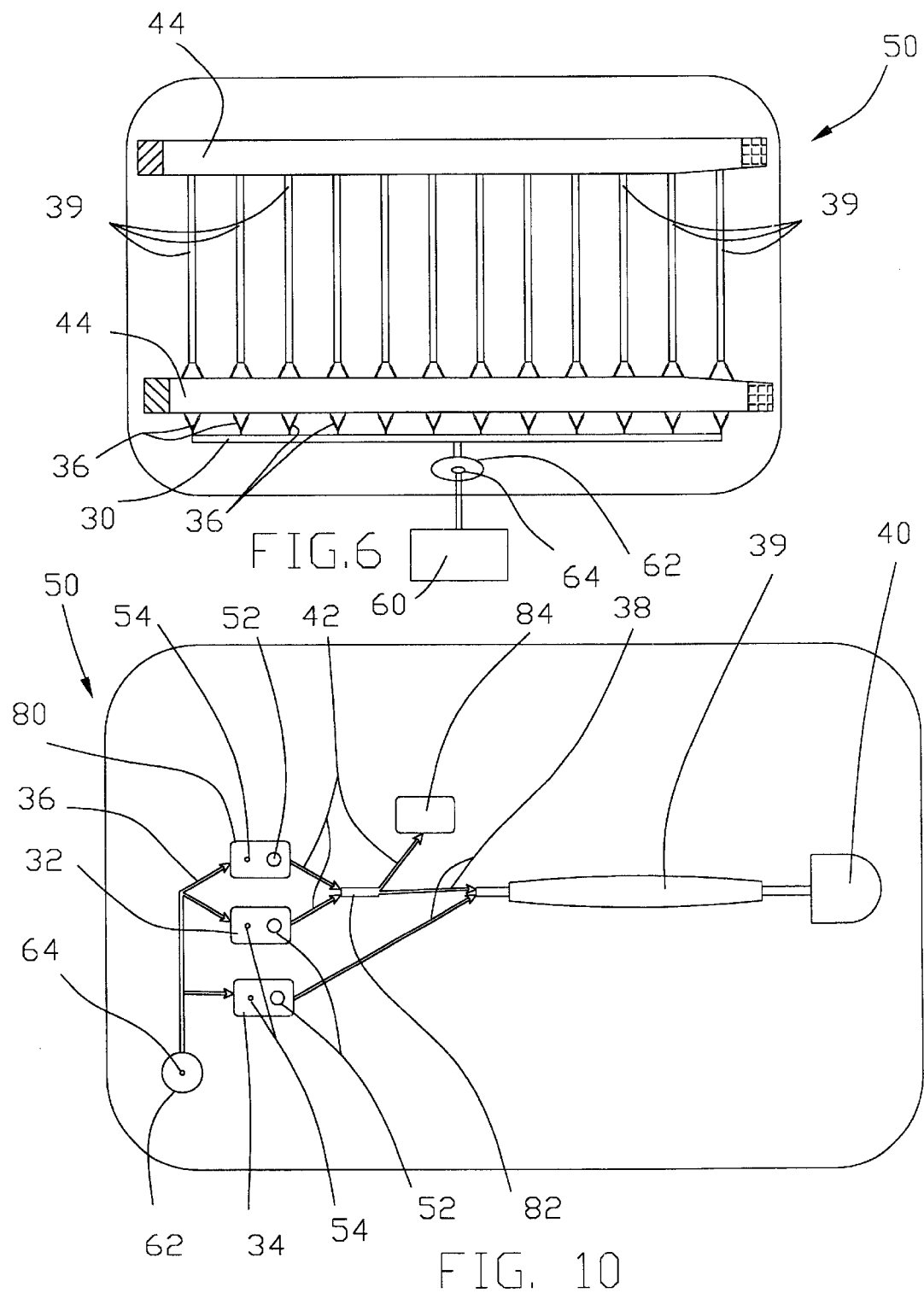

PROTEIN CRYSTALLIZATION IN MICROFLUIDIC STRUCTURES

CROSS-REFERENCE TO RELATED APPLICATIONS

This patent application takes priority from U.S. Provisional Application Ser. No. 60/193,867, filed Mar. 31, 2000, which application is incorporated herein in its entirety by reference.

BACKGROUND OF THE INVENTION

1. Field of the Invention

This invention relates generally to a device for growing crystals, and, more particularly, to a device for promoting protein crystal growth using microfluidic structures.

2. Description of the Related Art

Macromolecular crystals have become keystones of molecular biology, biochemistry, and biotechnology. Understanding how crystals express their function depends on knowledge of the macromolecular architecture at the atomic level.

The determination of the three dimensional atomic structure of crystals is one of the most important areas of pure and applied research. This field, known as X-ray crystallography, utilizes the diffraction of X-rays from crystals in order to determine the precise arrangement of atoms within the crystal. The result may reveal the atomic structure of substances as varied as metal alloys to the structure of deoxyribonucleic acid (DNA). The limiting step in all of these areas of research involves the growth of a suitable crystalline sample.

One important and rapidly growing field of crystallography is protein crystallography. Proteins are polymers of amino acids and contain thousands of atoms in each molecule. Considering that there are 20 essential amino acids in nature, one can see that there exists virtually an inexhaustible number of combinations of amino acids to form protein molecules. Inherent in the amino acid sequence or primary structure is the information necessary to predict the three dimensional structure. Unfortunately, science has not yet progressed to the level where this information can be obtained quickly and easily. Although considerable advances are being made in the area of high field nuclear magnetic resonance, at the present time the only method capable of producing a highly accurate three dimensional structure of a protein is by the application of X-ray crystallography. This requires the growth of reasonably ordered protein crystals (crystals which diffract X-rays to at least 3.0 angstroms resolution or less), as the accuracy of structures determined by X-ray crystallography is limited by the disorder in the crystallized protein.

The maximum extent of a diffraction pattern is generally considered to be a function of the inherent statistical disorder of the molecules of protein crystals rather than the result of purely thermal effects. Statistical disorder present in protein crystals has two principal sources: 1) intrinsic structural or conformational variability of protein molecules, and 2) spatial distribution of the individual molecules about lattice sites occupied.

In addition, other inherent limitations in the crystallization process involve the effects of molecular convection, thermal effects, and buoyancy, all due to the earth's gravitational field. Therefore, it has been proposed to conduct crystallization experiments in the microgravity ($1/1000$ g to $1/10,000$ g) of space, on board the space shuttle, international space station, or other similar vehicles. Several patents disclose crystallization in microgravity to improve the size, morphology and diffraction quality of crystals. U.S. Pat. Nos. 5,362,325 and 4,755,363 are exemplary of patents disclosing microgravity crystallization.

Focus of microgravity research in protein crystal growth (PCG) has been based on the observation that PCG in a microgravity environment yields protein crystals that are of reduced disorder. Reduction in lattice disorder by protein crystals grown in microgravity compared to ground controls offers enhanced resolution of diffracted intensities and translates at the atomic level into more precise knowledge of the protein architecture. The detailed knowledge of how ligands interact with binding sites at the atomic level permits insight into catalytic mechanisms and recognition in biological systems, a prerequisite for structure-assisted drug design. In a pharmaceutical industry setting, higher resolution implies significant manpower reduction in synthetic chemistry to explore the drug-binding site and results in more rapid optimization of drug target interaction. Accelerated drug design is extremely cost effective, allowing a pharmaceutical company to quickly recover R&D costs and improve profitability.

Several important advances have recently accelerated the structure determination process using even small crystals. These include selenomethionyl proteins, cryo-crystallography, high intensity synchrotron radiation sources, CCD detectors, and multiwavelength anomalous diffraction (MAD) phasing. With these advances, a protein structure can be solved by MAD phasing literally within hours of data collection at a synchrotron radiation source. The outstanding uncertainty faced by protein crystallography is the growth of high quality protein crystals.

In the very near future, it is expected that the field of structural genomics will foster a tremendous explosion in demand for protein structure determination. Genome sequencing or genomics is significantly impacting biological research by changing our understanding of biological processes through identification of novel proteins that may be involved in disease or are unique to pathogenic organisms. Genome project results have shown that in most organisms, more than 50% of the proteins have no assigned function. In the human genome, this amounts to over 50,000 proteins. These uncharacterized proteins thus represent a reservoir of untapped biological information that is widely acknowledged as the next generation of protein therapeutics and targets for pharmaceutical development. With large-scale genomic sequencing now becoming routine, attention is being focused on understanding the structure and function of these biological macromolecules. Recently published examples where knowledge of a three-dimensional structure of an unknown protein can provide clues to its function is expected to open the gates to a massive need for high quality structure determination.

The crystallization process generally involves several distinct phases, such as nucleation and post-nucleation growth. Nucleation is the initial formation of an ordered grouping of a few protein molecules, while post-nucleation growth consists of the addition of protein molecules to the growing faces of the crystal lattice and requires lower concentrations than the nucleation phase.

Most protein crystals nucleate at very high levels of supersaturation, typically reaching up to 1000% in many cases. At such supersaturation levels, post-nucleation crystal growth takes place under very unfavorable conditions. Most macromolecules at the concentrations needed to attain the very high levels of supersaturation tend to form aggregates and clusters of both ordered oligomeric species and/or random amorphous aggregates. Depending on the half-life and concentration of such clusters, formation of nuclei can involve incorporation of partially ordered aggregated species. Quiescent conditions mitigate imperfect post-nucleation growth at high supersaturation by reducing the collision frequency of aggregate species of all kinds to form larger clusters or nuclei. Microseeding a protein solution, that is, introduction of freshly crushed crystallites, would provide a succinct approach to circumvent growth from imperfect nuclei.

At higher levels of supersaturation, growth by absorption of three-dimensional nuclei onto crystal faces has been observed in crystallization studies of thaumatin, catalase, t-RNA, lysozyme, lipase, STMV virus and canavalin. The three-dimensional nuclei have observed average dimensions ranging between 1–10 $\mu$m making them colloidal in size. The origin of these nuclei is thought to be protein clusters that originate from protein rich droplets possessing short-range internal order and that undergo long-range ordering upon interaction with the underlying crystal lattice.

Under quiescent conditions at low supersaturation, a protein crystal grows by incorporation of individual protein molecules, monomers, from the surrounding medium, which because of their low diffusivities produce a concentration gradient or depletion zone about the growing crystallite. For lysozyme, protein concentration gradients measured by Mach-Zender interferometry surrounding a large 1 mm crystal are the order of ~10% over a 2–3 mm distance. Larger aggregates in the bulk solution diffuse more slowly than protein monomers, allowing the depletion zone to kinetically discriminate against incorporation of large aggregates into the crystal lattice. In effect, the depletion zone acts much like a mass filter. The depletion zone not only tends to filter out larger aggregates but also partially unfolded or denatured proteins which also have larger hydrodynamic radii, hence lower diffusivities than the compact globular native protein. Since mass filtering is transient and based on differential diffusion of the various species, protein crystal growth will eventually be compromised by self-impurities as the system approaches equilibrium. AFM studies in ground controls have shown that macromolecular crystals tend to stop growing because of formation of a dense impurity adsorption layer of protein restricting access to crystal faces.

In microgravity, sedimentation and buoyancy convection effects are suppressed and diffusion is the dominant mechanism of protein transport. Hence, a depletion zone would be extended and could more effectively exclude higher order protein aggregates from incorporation into a growing protein crystal, thus leading to a greater degree in crystal perfection. Recent PCG studies in microgravity with lysozyme dimer self-impurities tend to support this hypothesis. Non-quiescent conditions such as gravity induced sedimentation of larger nuclei and/or crystallites adjacent to the growing crystal would create disturbances in the depletion zone, facilitating incorporation of higher concentrations of self-impurities, and compromise its role of mass filtering. Post-nucleation growth by absorption of three-dimensional nuclei, observed at higher supersaturation levels, is particularly susceptible to sedimentation effects and buoyancy-driven flow. Particles such as nuclei of colloidal size are susceptible to gravitational effects and this may be in large part the basis for the beneficial effect of microgravity on PCG.

Frequently, prior to activation of a PCG experiment in microgravity, purified protein is stored at high concentration for as long as several weeks. For a protein maintained in soluble state, protein instability or unfolding promotes production of irreversible aggregates. Thus, given the high supersaturation conditions required for nucleation, protein crystal nuclei may contain significant concentrations of amorphous aggregates. Whether presence of self-impurities is detrimental to subsequent ordered post-nucleation growth and hence crystal quality is a function of the ability of competent nuclei to promote post-nucleation growth and concentration of competent monomeric species. Clearly, highly ordered nuclei tend to be kinetically more stable than amorphous aggregates, which is essential for sustaining post-nucleation growth. However, under prolonged solution storage, irreversible protein aggregation may compromise PCG success.

Several methods of protein crystallization have been developed and successfully employed over the course of the last century. These include vapor phase diffusion, liquid-liquid interfacial diffusion, liquid-liquid turbulent mixing, and step gradient methods.

Approximately 90% of protein crystallization experiments in microgravity (and on the ground) in the past decade have used the vapor diffusion or hanging drop method, in which water is transported through the vapor phase from a drop of protein and precipitant solution to a concentrated precipitant solution. This method has several advantages, especially at 1×g, including the relative absence of container surfaces, slow approach to supersaturation, low volume requirement, and ease of observation of crystal nucleation and growth, and it is fairly viscosity independent. It also has a number of disadvantages, including limited volume in the case of hanging (but not sessile) drops, limited control over saturation rate, and a potential for the establishment of convection currents at the liquid-air interface. The sessile-hanging drop, like the hanging-drop method, removes water only from the crystal-growth solutions. Unlike hanging drop in the sessile drop method, buoyancy-driven fluid upwelling often occurs, and the rate of water removal depends on vapor pressure. Examples of devices which use the vapor-diffusion method include U.S. Pat. Nos. 4,886,646; 5,103,531; 5,096,676; and 5,130,105.

Interfacial diffusion or liquid-liquid interfacial diffusion as a technique for protein crystal growth involves superposition of protein and precipitant solutions across an interface. PCG then depends on mutual self-diffusion of protein and precipitant across the resultant interface to grow protein crystals. Due to convection effects, such interfaces are not stable on earth but can be reproducibly generated in microgravity. The transient concentration gradient affords control over nucleation events by spatially reducing the number of nucleation sites. Protein dilution by the precipitant solution as system equilibration takes place diminishes the potential for protein aggregate incorporation into nuclei and crystallites. In this method, a depletion zone will only be established once the system has approached equilibrium. Mixing of highly viscous fluids by interfacial diffusion occurs very slowly and can correspond to a time scale incompatible with the duration of a shuttle mission but is compatible with the ISS mission.

Turbulent mixing will result essentially in the system being brought to its equilibrium value at the onset of the PCG experiment and maintained at equilibrium throughout the experiment. This is useful in allowing comparisons to be made where it is important to know the final end point of a system and is akin to batch crystallization. Turbulent mixing also overcomes difficulties associated with mixing of viscous precipitants.

In the step gradient approach, homogeneous nucleation and crystal growth are treated as separate steps. Homogeneous nucleation is induced by bringing, carefully, a near saturated protein solution into contact with a highly super-saturating solution of precipitant (1.2–3.0 times saturating concentration, for example). This exposure lasts just long enough to cause nucleation, then the crystals are transferred to a slightly saturating concentration of precipitant for quiescent crystal growth. This method has been successfully used to grow protein crystals in space.

An essential difference between vapor phase diffusion and liquid-liquid interfacial diffusion is in their mutually orthogonal approach to equilibrium in the protein solubility phase. Vapor diffusion starts from a dilute protein solution that becomes concentrated at equilibrium, while liquid-liquid interfacial diffusion dilutes the protein starting condition.

All of the methods discussed above have gravity-dependent components. Crystals more dense than the mother liquor sediment away from the zone of crystallization, while those less dense float away from this zone. Sedimentation against a vessel wall modifies the habit of the crystal. Rapid nucleation on a dialysis membrane or vessel wall sometimes leads to large numbers of small crystals. Ideally, motionless, contactless crystal growth is desired, and the microgravity environment of space flight comes very close to providing these conditions.

Modern protein crystallography data collection techniques make use of protein crystals flash frozen in liquid nitrogen to minimize radiation damage. Crystals of large dimensions (0.5–1 mm) are more readily damaged during flash freezing while smaller crystals (~0.2 mm or less in average dimension) can be cooled rapidly enough to prevent ice formation. Using $2^{nd}$ and $3^{rd}$ generation synchrotron radiation sources and CCD detectors, even smaller crystals have been successfully exploited. The device of the present invention thus targets growth of high quality small and medium size crystals. The presence of self-impurities is more likely to compromise growth of larger crystals than smaller crystals largely in part to the longer time scale involved for growth of large crystals, making them more susceptible to protein denaturation phenomena.

Protein denaturation, if it does occur prior to PCG activation in microgravity, can compromise PCG success by formation of irreversible aggregates, self-impurities, in the protein solution. If irreversible aggregation does take place in ground experiments and compromises PCG success, the facility should be able to mitigate against the protein aggregate population at the time of PCG activation.

Protein crystals can be stressed or even damaged during harvesting and/or in subsequent manipulations and therefore become unsuitable for data collection. The present device should allow facile harvesting of protein crystals for flash freezing. In particular, potential crystal entrapment in corners should be avoided.

The device should afford facile integration and dispersement of large number of PCG experiments by a PCG mission integration center as well as allow ready documentation of post-flight results.

The PCG experiment should allow for crystallization in small volumes comparable to volumes ($\mu L$) used in routine laboratory PCG screening, thus consuming as little protein as possible.

Technically, the facility should provide efficient separation of protein and precipitant prior to orbit activation with no absorption and leakage of fluids over the course of the microgravity mission.

Microfluidic devices have been recognized to have great potential in such areas as DNA sequencing and medical diagnostics. Beyond this, they have the potential to allow separations, chemical reactions, and calibration-free analytical measurements to be performed directly on very small quantities of complex samples such as whole blood and contaminated environmental samples. Therefore, use of disposable microfluidic devices should be investigated as means for growing protein crystals in microgravity.

The embodiment of the technology uses microfluidic integrated circuits. These devices are thin transparent plastic or glass structures, roughly credit card in size. Laminar flow structures in these chips afford crystal growth by free liquid-liquid interface diffusion, batch methods, or vapor diffusion, depending on circuit design. The chips are readily loaded with fluid samples, which, manufactured from transparent material, allow facile documentation of PCG results and also permit facile unloading and harvesting of protein crystals grown.

Most fluids show laminar behavior in miniature flow structures with channel cross sections below 0.5 mm. Two or more distinct fluid streams moving in such flow structures do not develop turbulence at the interface between them or at the interface with the capillary walls. Different layers of miscible fluids and particles can thus flow next to each other in a microchannel without any interaction, other than by diffusion of their constituent molecular and particulate components. Microfluidic channels typically have either width or height less than ~500 $\mu$m. Liquids with viscosities comparable to water or that flow slower than several cm/sec follow predictable laminar paths. These conditions correspond to values of the non-dimensional Reynolds numbers of ~1 or less. The Reynolds number characterizes the tendency of a flowing liquid to develop turbulence; values greater than 2000 indicate turbulent flow. Values between 1 and 2000 allow for so-called laminar recirculation, which is frequently used in microfluidic mixing structures.

Recent advances in device miniaturization have led to the development of integrated microfluidic devices, so-called labs-on-a-chip. In these tiny microchips etched with grooves and chambers, a multitude of chemical and physical processes for both chemical analysis and synthesis can occur. These devices, also known as micro-total analysis systems ($\mu$TAS), can be mass produced in silicon by techniques similar to those used in the semiconductor industry, or, for even lower cost, made out of plastics by using casting, cutting, and stamping techniques. Recent advances in microfabrication have extended the production of these devices to include a wide range of materials. They offer many advantages over traditional analytical devices: they consume extremely low volumes of both samples and reagents. Each chip is inexpensive and small. The sampling-to-result time is extremely short. In addition, because of the unique characteristics exhibited by fluids flowing in microchannels ("microfluidics"), it is possible that these designs of analytical devices and assay formats would not function on a macroscale. For PCG, microfluidic structures offer a novel, innovative and modular concept different from the current available PCG hardware. There are a number of ways in which these microfluidic structures are relevant to PCG.

Several microfluidic structures have been recently developed which can be useful as "building blocks" for a variety of different disposable crystallization chips. These devices make it possible to deliver small volumes (tens of nanoliters to tens of microliters) of sample and reagents at flow rates down to nanoliters per second.

Due to the low Reynolds Number conditions in microfluidic systems, mixing is usually limited to laminar diffusion mixing or laminar recirculating mixing. However, it is possible to introduce turbulence into microfluidic systems. Devices have been developed which allow quasi-turbulent mixing of both two or more single-phase liquids or liquids containing solid particles. It consists of a series of chambers, connected by small-diameter channels. Once the mixer is filled, the fluid contained in the mixer can be subjected to a series of reversals of direction. Each time the fluid is pulsed in the forward or reverse direction, each tangential channel produces a laminar jet in each chamber. Because each laminar jet causes the fluid in each chamber to rotate as a vortex in the same direction, the rotational shear field induces mixing. Fluid mixing can also be achieved by separately dividing each fluid channel into narrow finger channels and then recombining the all finger channels into one channel.

U.S. Pat. Nos. 5,716,852 and 5,932,100 are directed to microfluidic structures which operate on the principle of laminar flow within a microscale channel wherein separate input streams are placed in laminar contact within a single flow channel such that desired particles can be detected or extracted by virtue of diffusion. U.S. Pat. No. 5,716,852, which patent is hereby incorporated by reference, discloses a device, known as a T-Sensor, which can be used to analyze the presence and concentration of small particles in streams containing both small particles and larger ones by diffusion principles. The speed of the diffusion mixing is a function of the size of the diffusion particles. U.S. Pat. No. 5,932,100, which also is hereby incorporated by reference, discloses a device known as an H-Filter, which, by laminar flow, allows separation of particles based on diffusion coefficients on a continuous basis without the need for semipermeable membranes. The H-Filter can also be used as a dilution tool, or, by using several H-Filters in series, a highly accurate serial dilution structure.

Although not directly related to the concept study, understanding of a T-Sensor operation is necessary for appreciation of the PCG concept design. A T-Sensor is a micro-total analysis system ($\mu$TAS) component that combines the separation features of the H-Filter with detection. A T-Sensor system is demonstrated in which a sample solution, an indicator solution, and a reference solution are introduced in a common channel. The fluids interact during parallel flow until they exit the microstructure. Large particles such as blood cells would not diffuse significantly within the time the flow streams are in contact. Small atoms such as $H^+$, $Na^+$, and small molecules diffuse rapidly between streams, whereas larger polymers diffuse more slowly and equilibrate between streams further from the point of entry to the device. As interdiffusion proceeds, interaction zones are formed in which sample and reagents may bind and react. T-Sensors can be used to let components from two different, but miscible streams diffuse into one another and react with each other. For example, antigens contained in one stream can diffuse into a parallel stream containing antigens, and react with them, while the two original streams remain largely separate.

T-Sensor-like structures can be used to induce precipitation or crystallization of sample components. For example, components from one stream can diffuse into a parallel stream and react with a component there to form a precipitate. Alternatively, solvent molecules from one stream can diffuse into a parallel stream containing a different solvent and particles. The change in solvent properties along the diffusion interface zone can then induce crystallization or precipitation. Obviously, it is also possible to apply a temperature gradient to a microchannel, either across the channel or along its flow direction, and affect the precipitation characteristics this way. Microseeding would be another possibility with this device.

It should be noted that it is possible to mitigate against protein instability using microfluidic technology. Protein denaturation results in polydisperse protein populations that contain higher order protein aggregates. The concentration of these aggregates can be minimized or even eliminated through use of an H-filter structure because of the difference in diffusion coefficients between native protein and protein aggregates. An H-filter set up, would preferentially concentrate the monodisperse native protein in the filter output.

Another microfluidic device which may be useful with respect to PCG is described in U.S. Pat. No. 5,726,751, which patent is hereby incorporated by reference. This patent discloses a device, known as a microcytometer, which is based on a sheath flow cytometer design, and has at its heart a disposable laminate cartridge technology developed specifically for microfluidic devices. It may be possible using this technology to focus precipitating crystals using a combination of microfluidic hydrodynamic and geometric focusing structures. This would line up the particles in a single file as they flow past a detector, or allow them to settle out on the bottom of the structure in a very controlled and precise way.

Finally, several other devices which were developed in view of microfluidic technology are taught in U.S. Pat. Nos. 5,474,349; 5,726,404; 5,971,158; 5,974,867; 6,007,775; 5,948,684; and 5,922,210; these patents are also hereby incorporated by reference into the present application.

SUMMARY OF THE INVENTION

Accordingly, it is an object of the present invention to provide a device for growing protein crystals using microfluidic structures.

It is also an object of the present invention to provide a device in which multiple assays can be performed simultaneously.

It is a further object of the present invention to provide a device in which small volumes of liquids can be used to perform protein crystal growth (PCG) experimentation.

It is a still further object of the present invention to provide a device which is easy to use under microgravity conditions.

These and other objects and advantages of the present invention will be readily apparent in the description that follows.

BRIEF DESCRIPTION OF THE DRAWINGS

FIG. 6 is a top view of the cartridge of FIG. 5 shown in the activation mode;

FIG. 10 is a top view showing the loading mode of a microfluidic cartridge showing another embodiment for carrying out the present invention.

DETAILED DESCRIPTION OF THE PREFERRED EMBODIMENTS

Figure 8:
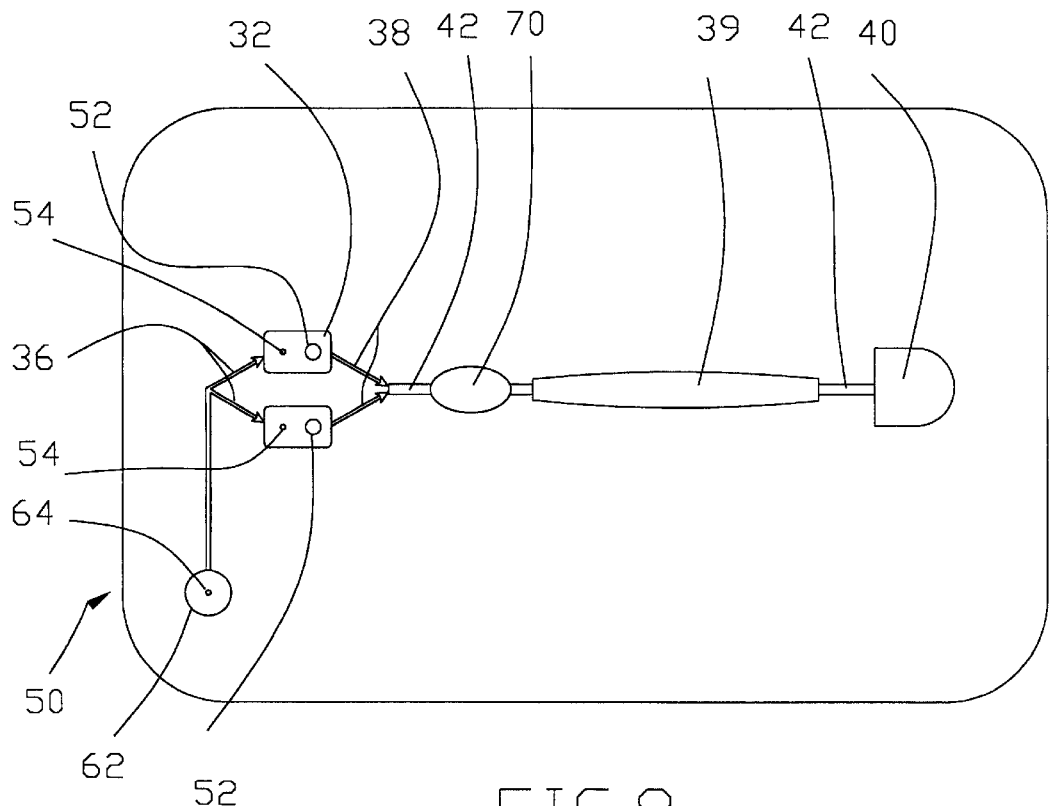
FIG. 8 is a top view showing the loading mode of a microfluidic cartridge showing another embodiment for carrying out the present invention.

Solution conditions that promote ordered protein aggregation are favorable for protein crystallization. Aggregation involves protein interactions mediated through specific forces that are sensitive to protein surface topology and chemical identity of the surface groups. The complexity of these interactions represent the difficulty encountered in obtaining X-ray diffraction quality crystals. While developed for very simple particle interactions, statistical mechanical models of order/disorder phase transitions have offered insights into how to characterize the effect of solution conditions on solubility. Attempts to characterize proteins as simple fluids suggest that, under most crystallization conditions, proteins experience attractions, which have a range much shorter than their size. This has important consequences on protein solution phase behavior. First, the solubility at a given strength of attraction becomes weakly dependent on the extent of the attraction. Consequently, large classes of proteins can display a narrow range of solubility at a given level of attraction and on which protein crystallization is dependent.

One method of characterizing the strength of the attraction is to measure the protein $2^{nd}$ virial coefficient. A second consequence of the short-range nature of the interaction potential is that protein solutions will show through density fluctuations a metastable fluid/fluid phase transition. This transition appears as a phase separation into two solutions: one rich in protein and one dilute in protein. The critical point for this phase transition lies at stronger attractions than the fluid/crystal phase boundary. Therefore, crystals will ultimately grow from the protein rich phase-separated state. The proximity of the critical point to the fluid/crystal phase boundary plays an important role in crystal nucleation and which is linked to the narrow range of the protein $2^{nd}$ virial coefficient values consistent with protein crystallization. The role of additives or different starting conditions is to modify fluid/fluid phase boundaries and create solution conditions favorable for protein crystallization.

Interaction between protein molecules is concentration dependent and can be assayed from light scattering measurements. The dependence of a light scattering on protein concentration in dilute protein solutions is directly informative as to the extent of protein interaction and the constant characterizing this dependence is the $2^{nd}$ virial coefficient, $B_2$. Positive values for $B_2$ are qualitatively representative of repulsion between protein molecules while negative values indicate attractive interactions between protein molecules. Large negative values of $B_2$ imply strong attractions between protein molecules that result in gel formation or amorphous precipitation. George and Wilson observed that there was a commonality to the solution conditions that are favorable for protein crystallization, and that commonality could be expressed by the $2^{nd}$ virial coefficient, $B_2$. The measured values for $B_2$ using many different protein-solvent pairs all, unambiguously, fall into a fairly narrow range referred to as the crystallization slot. This slot is an empirical representation of solution conditions for which PCG was successful. The $B_2$ values comprising the slot are slightly to moderately negative ($\approx -1$ to $-8 \times 10^{-4}$ mol ml g$^{-2}$) and represent slightly to moderately net attractive forces between protein molecules.

Static light scattering (SLS) is the analytical method used to determine the $2^{nd}$ virial coefficient, $B_2$. This method requires the intensity of light scattered by a protein solution in excess of background due to solvent and stray light to be measured as a function of the protein concentration. The working relationship used to analyze the SLS data is given by the following equation:

$$\frac{K_C}{R_\theta} = \frac{1}{M} + 2B_2 c + ...$$

where K is an optical constant dependent on refractive index, Avogadro number, wavelength of incident light and change of refractive index with protein concentration c. The excess Rayleigh ratio, $R_\theta$, measured at a scattering angle of $\theta$ is determined as a function of protein concentration c. M represents the molecular weight. By plotting $Kc/R_\theta$ versus c, the $2^{nd}$ virial coefficient, $B_2$, can be obtained from the limiting slope. $B_2$ is a dilute solution parameter and the protein concentration used for the SLS data depends on detection sensitivity, ranges are typically 0.05 mg/ml for proteins of large molecular weight to 1 mg/ml for lysozyme. In comparison to protein concentrations used for PCG, the $2^{nd}$ virial coefficient can be determined using small quantities of protein.

Surfactants are required to solubilize membrane proteins. Therefore, in order to crystallize a membrane protein one must crystallize the complex of protein bound to the surfactant used. Most membrane protein crystals to date have been observed to form near the cloud point of the surfactant used. This cloud point is the surfactant phase separation boundary corresponding to the aggregation of surfactant micelles; as a solution approaches the cloudpoint, intermicellar potentials switch from repulsive to attractive. As static light scattering is sensitive to micellar structures, determination of the second osmotic virial coefficient ($B_2$) for the protein-surfactant complex must take into account the interactions between scattering micelles. A T-sensor detection structure described below allows measurement of the second osmotic virial coefficient for the protein-surfactant complex in presence of the surfactant micelles.

Although the value of the $2^{nd}$ virial coefficient is predictive of crystallization conditions, not all starting condition consistent with a crystallization slot value for the $2^{nd}$ virial coefficient guarantee diffraction quality crystals. Hence the value of $2^{nd}$ virial coefficient will be used to filter starting conditions, conducive for PCG trials, and all conditions will be screened that correspond to weakly attractive protein interactions that bracket the $B_2$ crystallization slot value.

Two general types of "gravity-driven" microfluidic structures have been manufactured: the "vertical" (GVT and GVH) types, which have integrated sample and reagent reservoirs, and which are operated vertically or at an incline, and the "horizontal" (GHT and GHH) types, which have tubes attached to them for sample and reagent filling. The letter code stands for Gravity-driven Horizontal (or Vertical) H-Filter (or T-Sensor). H-Filters have two inlets and two outlets, are designed to separate components of a sample solution, and allow the collection of the output solutions. T-Sensors have two or three inlets, and only one waste outlet. They allow the detection of analytes directly in complex sample solutions (such as whole blood). They are filled with a sample solution, a indicator solution, and, for three inlet-T-Sensors, an additional reference solution with a known concentration of analyte.

In both GH- and GV- type structures, the flow rate depends on the hydrostatic height of the flow column in each of the inlets, and each of the outlets. This means that the flow speed as well as the relative position of the centerline between the two streams can be adjusted by changing the height of the fluid column in each inlet and outlet. Some of the T-Sensor types are less sensitive to differences in the fluid column height; others are more sensitive, but these also allow to adjust the centerline very accurately.

Both GVT and GHT types can be filled with the "filling syringes". For GV-types, place the blunt needle inside the hole of the reservoirs on top of each cartridge. It is easiest if the needle is placed somewhat to the side of the hole, and the cartridge is held at a slight downward angle; fill slowly and carefully to avoid air bubbles. The reservoir does not need to be filled completely; however, the area close to the junction with the inlet channels must be covered with fluid.

Sometimes the flow starts as soon as the liquid is placed in the tube; if it is required that the fluids do not mix at all before they enter the main T-sensor channel, then all reservoirs should be filled while the GV cartridge lies flat. Filling GHT-type cartridges is somewhat easier; just fill sample and indicator into both inlet tubes at the same time and to the same level using two syringes or pipettes.

For both GH and GV types, frequently the flow does not start by itself when the fluids are in the tube or the inlet reservoirs. In this case, place the "aspiration syringe" with the silicon tip (enclosed) over the outlet channel opening and aspirate slightly until the fluids start flowing from all inlets. Keep aspirating until all air bubbles that may have formed are removed from the channels. Fluids should now flow unaided as a function of hydrostatic pressure alone.

The flow speed can be adjusted by adding or removing fluid from the inlet tubes (GH types), or by adjusting the incline of the cartridges (GV-types). The higher the height difference between inlet and outlet fluid levels, the faster the fluids will flow for a given structure. Alternatively, the flow can be increased by placing a Q-Tip on the outlet opening (once the fluid has reached the outlet), which increases the flow dramatically through absorptive action.

The following presents a description of certain specific embodiments of the present invention. However, the present invention can be embodied in a multitude of different ways as defined and covered by the claims. Throughout the drawings, like parts are designated with like index numerals throughout.

Figures 1, 2, 3:
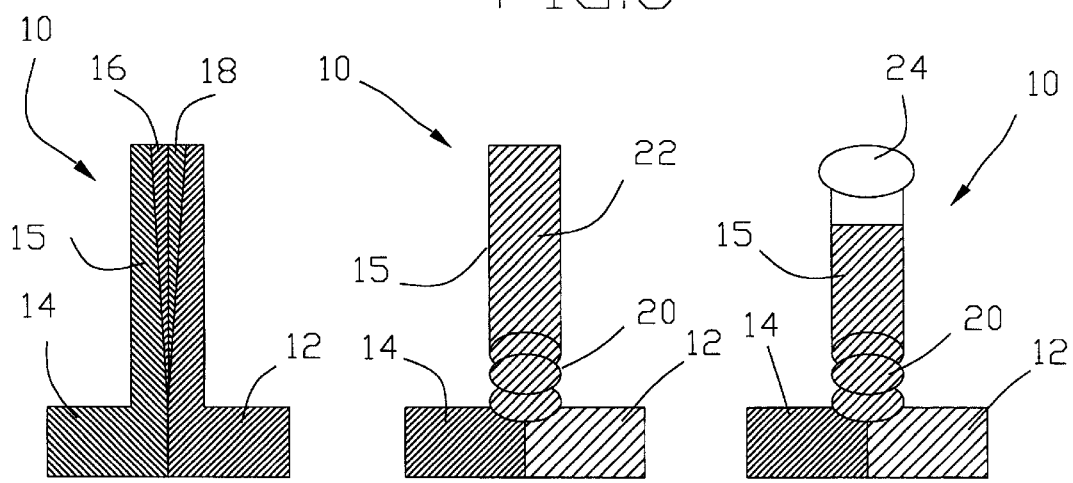
FIG. 1 is a graphic representation of a T-Sensor which may be used in the present invention.
FIG. 2 is a graphic representation of the T-Sensor of FIG. 1 in which the two input fluids are premixed.
FIG. 3 is a graphic representation of the T-Sensor of FIG. 2 which simulates the vapor phase or hanging drop diffusion method of protein crystallization.

A T-Sensor-like structure, generally indicated at 10, is shown in FIG. 1 to demonstrate the principles of diffusion-based crystallization. A sample 12 containing dissolved protein, and a reagent 14 containing a variety of different solvents and salts, flow together in parallel within a channel 15 of T-Sensor 10. After establishing a laminar flow profile, the flow is significantly slowed or stopped. The various components of both streams 12, 14 will now diffuse into each other at a certain rate, depending on the size of the molecules within these streams, forming diffusion interface zones 16, 18 within channel 15 of device 10. This action establishes a concentration gradient in device 10, which allows for a very well defined crystallization. Solvent molecules from one stream can diffuse into a parallel stream containing a different solvent and particles. The change in solvent properties along diffusion interface zones 16, 18 can then induce crystallization or precipitation. Obviously, it is also possible to apply a temperature gradient to a microchannel, either across the channel or along its flow direction, and affect the precipitation characteristics this way. Microseeding would be another possibility with this device.

Referring now to FIG. 2, a microfluidic rapid mixing structure 20, such as a laminar jet vortex mixer which is described in U.S. patent Ser. No. 60/206,878, a split-channel diffusion mixer, or any other mixer that rapidly mixes fluids in the low Reynolds-number regime can be placed upstream of crystallization channel 15. The protein sample and the reagent are mixed at a certain ratio, and then flow into crystallization channel 15, where a homogeneously mixed solution 22 is slowed or stopped. Crystallization will then occur inside channel 15. Again, microseeding or temperature gradients can also be applied.

Figures 4A, 4B:
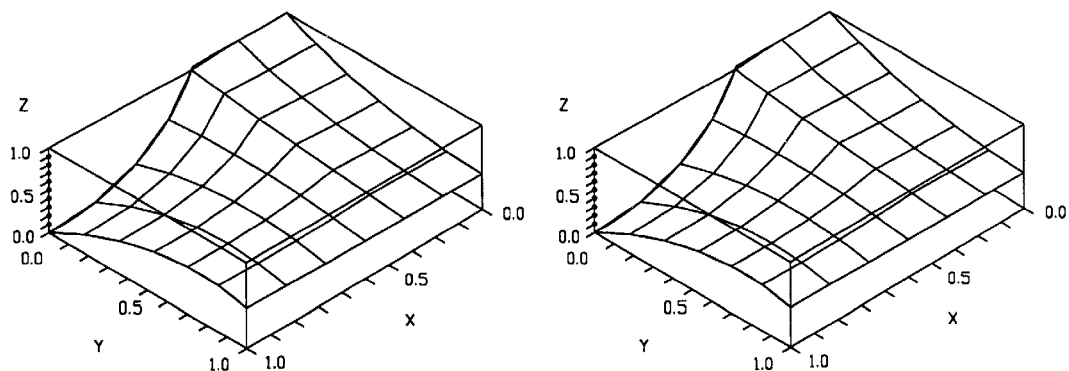
FIGS. 4A and B show graphic representations of several molecules which have been mixed in a diffusion mixer after an elapsed time period.

FIGS. 4A and 4B show the behavior of two different molecules when mixed using a diffusion mixer. The figures demonstrate that, within about 2 minutes, even large molecules are completely equilibrated across 100-micrometer wide channels that make up the split-channel diffusion mixer. FIG. 4A shows a phosvitin complex (1,490,000 MW) concentration (Z) in a 100 $\mu$m channel (X) for 120 seconds (Y), while FIG. 4B shows a thyrogobulin (bovine) (669,000 MW) concentration (Z) in a 100 $\mu$m channel (X) for 120 seconds (Y).

Referring now to FIG. 3, T-Sensor 10 of FIG. 2 is again used; but in this embodiment, crystallization channel 15 is filled only partially. Exit end of channel 15 is connected to an absorbing material 24 that absorbs, over time, a predefined quantity of solvent mixed solution from 22, thereby increasing the concentration of protein, and inducing it to crystallize. Again, microseeding or temperature gradients can also be applied in this embodiment.

Figure 5:
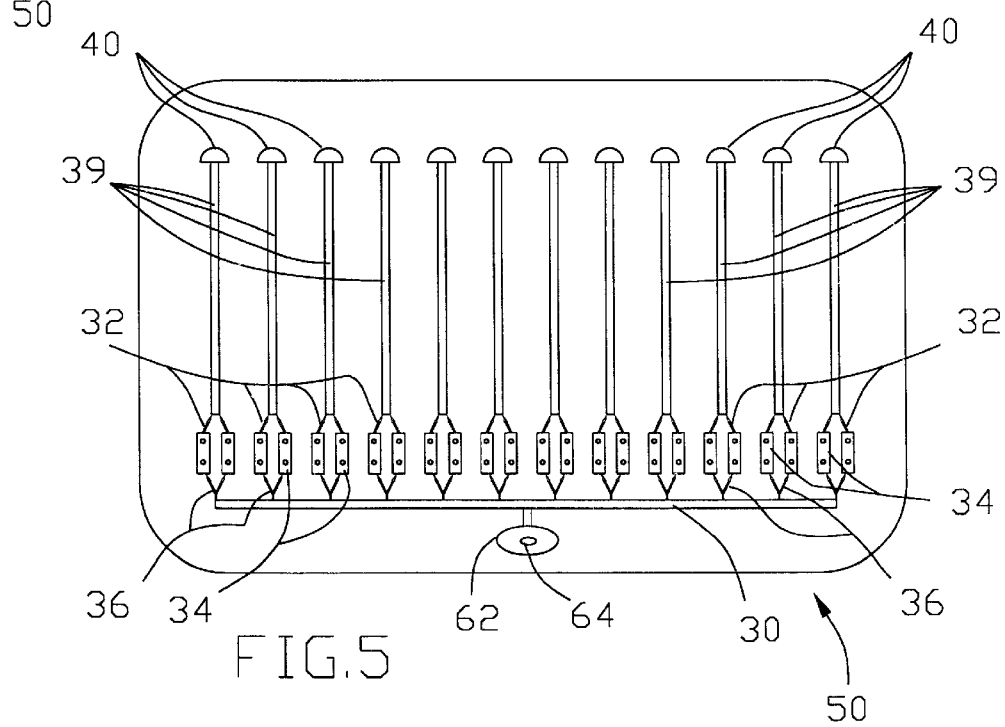
FIG. 5 is a top view of a microfluidic cartridge for use in the present invention shown in the loading mode.

A prototype for 12 PCG experiments on a single card is shown in two different operational modes in FIGS. 5 and 6. A single microfluidic PCG experiment embodies the following elements: a driver fluid interface 30, two fluid reservoirs 32, 34 and microfluidic channel/check valves 36, 38, crystallization chamber 39, harvesting chambers 40, microchannel connections 42 and adhesive sealing means 44.

Referring now to FIG. 5, a microfluidic cartridge, generally indicated at 50, contains a plurality of fluid reservoirs 32, 34. Reservoirs 32 are filled with a protein sample, while reservoirs 34 are filled with a precipitant solution. Fluids in reservoirs 32, 34 are expelled by applying pressure to a fluid located within channel 30, which may be air or an inert oil. Reservoirs 32, 34 combine to form a T-sensor structure with crystallization chamber 33. Laminar flow ensures that the two fluids do not mix within chamber 39 other than by mutual self-diffusion. The contents of crystallization chamber 39 void into harvesting chamber 40. Each fluid reservoir 32, 34 is filled through a fluid inlet 52 and has microfluidic channel/check valves 36, 38 a vent hole 54 to permit air escape during the filling operation. Surface tension effects because of the small diameter of the connecting to the fluid reservoirs 32, 34 prevent fluids flowing out of said reservoirs. Once loaded, fluid reservoirs 32, 34 are carefully sealed with adhesive strip 44, as can be seen in FIG. 6. This strip 44 can be supplied directly bonded to cartridge 50. Harvesting chambers 40 are sealed with another strip 44 of adhesive tape also supplied directly on cartridge 50. In microgravity or for long-term storage prior to fluid activation, the check valves 36, 38 minimize vapor loss from reservoirs 32, 34. Check valves 36, 38 allow fluid flow in one direction only such that back flow is prevented, and when appropriately placed within a microfluidic circuit, can act as one level of fluid containment.

External valve activation and fluid driving can be accomplished in one of two ways: using an external driver or by air bellows incorporated on the microfluidic cartridge. An external fluid driver interface 60 (FIG. 6) would be an air pump to which each card would be hooked up. Air pump 60 delivers a precise amount of pressure to drive fluids through the circuit. Another option is to use an air bellows 62, as shown in FIG. 5, directly manufactured on the circuit board that can be driven by pressure to pump the fluids into the microfluidic structures. Air bellows 62 may also have a vent hole 64, which may be sealed by a ball bearing, and when under pressure air bellows 62 would again act as the fluid driver. Release of pressure due to sudden power outage would allow air to bleed into the microfluidic circuit, allowing it to equilibrate. Check valves 36, 38 in any event would prevent fluid back flow and satisfy one level of containment. The advantage of vent hole 64 on the air bellows 62 is that circuit cartridge 50, once actuated, could be allowed to slowly return to equilibrium and then allow facile harvesting of crystal chamber 40 contents by applying another round of pressure on the bellows 62. It is also possible to fill bellows 62 with inert oil to drive the fluids and prevent vapor loss in the microfluidic cartridge 50 over the long-term course of a PCG experiment, if this becomes necessary.

Activation by applying pressure on the driver fluid within channel 30 by bellows 62 pumps the fluid reservoirs 32, 34 contents into crystallization chamber 39 via check valves 36, 38. Check valves 38 ensure that there is no back flow from crystallization chamber 39 while check valves 36 ensure a further level of fluid containment. Harvesting of a particular PCG experiment occurs by partially peeling off the adhesive strip 44 to allow access to the chosen harvesting chamber 40. Circuit pressurization via fluid driver interface 60 or air bellows 62 would allow flushing with inert oil or air of the crystallization chamber 39 contents. Crystals are then accessible for facile transfer and/or manipulation within harvesting chamber 40. Currently, a clear plastic adhesive tape commercially available from Hampton Research is used for sealing hanging drop experiments. This tape seals the equilibration wells while at the same time holding the hanging drop. This tape is compliant such that tape covering the crystal harvesting chambers 40 creates a minimal backpressure once fluid is pumped into the channel. Should compliance present a problem, it is possible to provide a narrow vent hole on the outlet side that is very hydrophobic, and therefore would not let any liquid escape, only air.

The prototype crystallization chip in the PCG device would incorporate the vented air bellows design. This greatly simplifies testing and makes it very user-friendly. For the device, a volume of 20 $\mu$L can be used for each crystallization chamber; however, smaller chamber volumes of 10–100 nanoliters are readily possible. Three approaches can be used in the microfluidic circuit cartridges to initiate protein crystallization and accompanying figures show the conceptual design for a single PCG experiment on the prototype board. It should be noted that all three approaches could be mixed and matched onto a single board. The PCG techniques are: self-diffusion of precipitants and protein across a laminar boundary (see FIG. 7); turbulent mixing of all components—batch mode (see FIG. 8); and vapor transport into a desiccant or precipitant (see FIG. 9).

Figure 7:
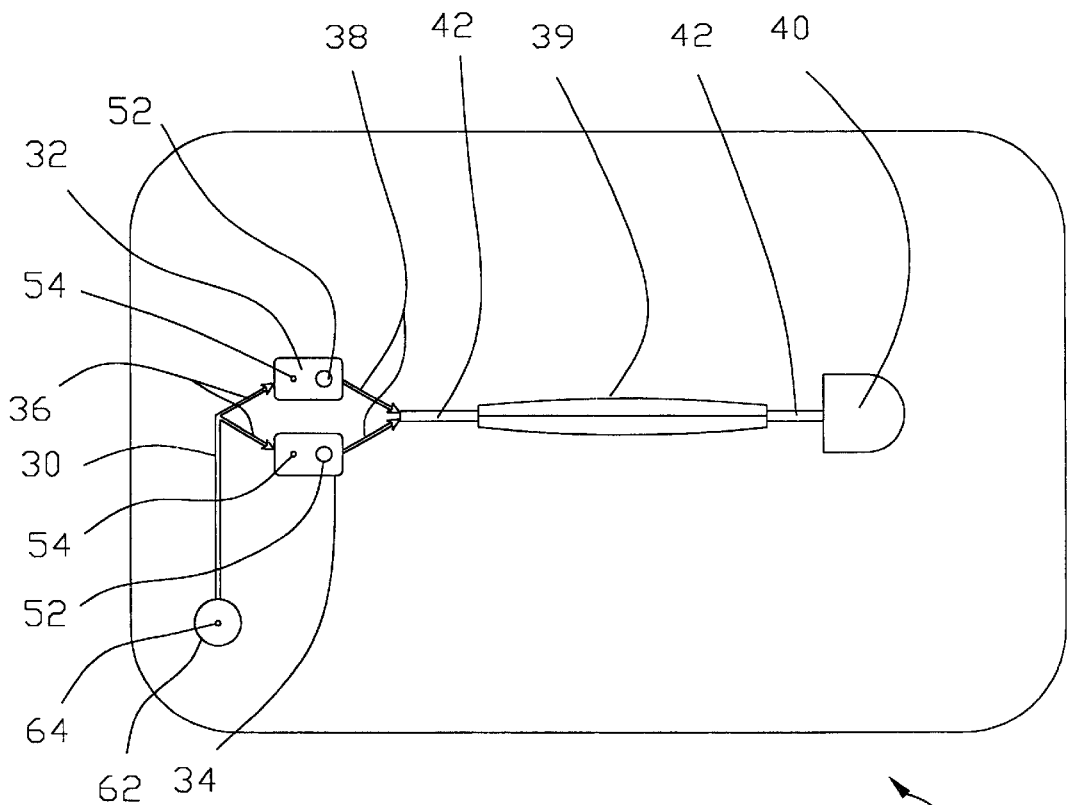
FIG. 7 is a top view showing the loading mode of a microfluidic cartridge showing another embodiment for carrying out the present invention.

Referring now to FIG. 7, the interfacial diffusion approach will consist of using 2×concentrations of protein and precipitant in each fluid reservoir (volumes>10 $\mu$L) and each made up in 1×concentrations of same buffer, salt and detergent. The two fluids are then injected under pressure in a 1:1 mixing ratio controlled by the diameter of microchannels 42 into crystallization chamber 39. Chamber can be filled under laminar flow conditions provided that it has at least one dimension of less than roughly 500 micrometers, and chamber is filled fairly slowly using gentle finger pressure (all other microfluidic structures will be small enough to easily fulfill the requirements of laminar flow). Pressure in the system is equilibrated by removing the finger gently from vent hole 64. Air bellows 62 are then carefully sealed with clear adhesive tape in the same way as are fluid reservoirs 32, 34 and harvesting chamber 40. Voiding of crystallization chamber 40 into harvesting chamber 40 involves removal of the adhesive tape covering harvesting chamber 39 and applying pressure on air bellows 62.

Referring now to FIG. 8, cartridge 50, which uses turbulent mixing for all components, operates in a batch mode. A turbulent mixing chamber 70 is inserted between fluid reservoirs 32, 34 and crystallization chamber 39. Chamber 70 mixes the protein and precipitant fluids into a homogeneous liquid which is transported to chamber 39 for crystallization. This design is particularly useful under microgravity conditions such as on a space shuttle mission, as the viscous precipitants do not have time to mix and induce nucleation during the duration of an extended mission.

Figure 9:
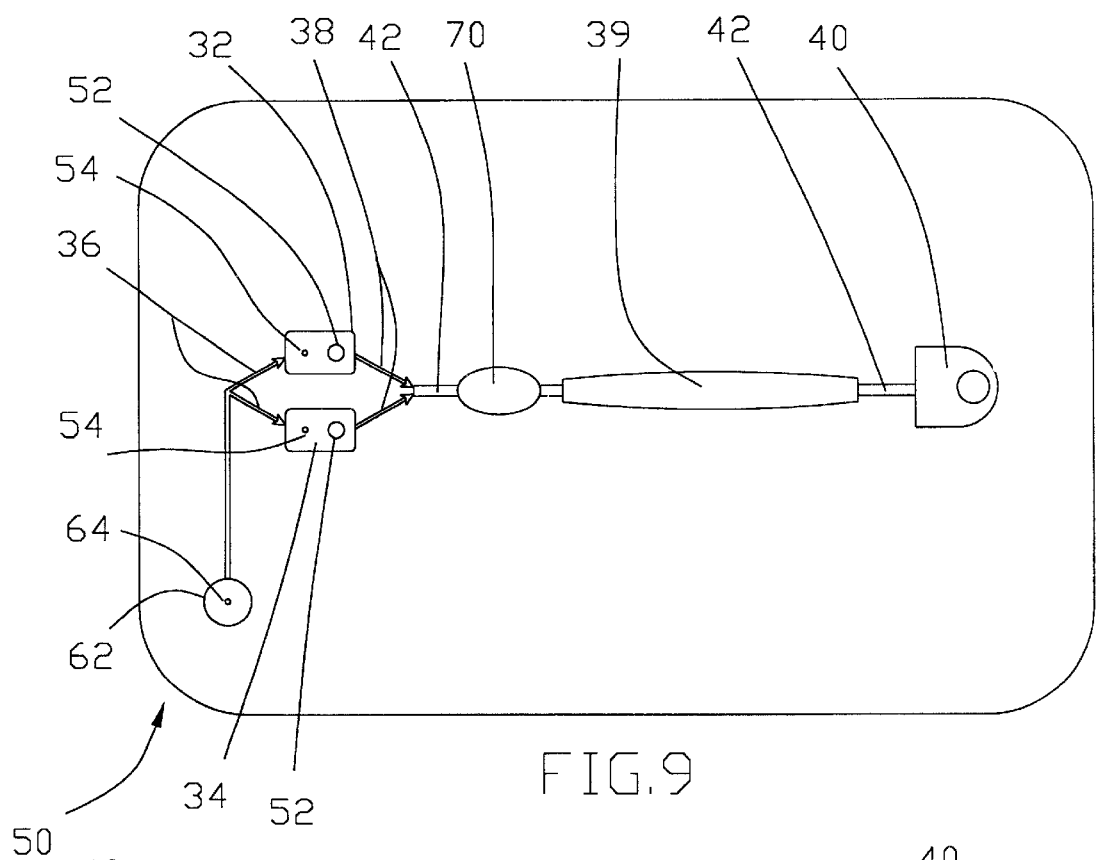
FIG. 9 is a top view showing the loading mode of a microfluidic cartridge showing another embodiment for carrying out the present invention.

FIG. 9 shows an example of cartridge 50 of FIG. 8 which uses the principles of vapor diffusion to operate. In this embodiment, crystallization chamber 39 is only partially filled after the fluids are mixed within mixing chamber 70. A predefined desiccant or precipitant 72 is located within harvesting chamber 40 to absorb a fixing quantity of solution into chamber 40, increasing the concentration of protein with chamber 39, and inducing crystallization.

It would also be possible to take a starting protein solution and dialyze it against the appropriate starting fluid composition using an H-Filter prior to the crystallization experiment, should long term in-orbit storage in a particular buffer be deleterious to protein stability. An H-filter setup could be incorporated into the design to eliminate irreversible protein aggregates. Referring now to FIG. 10, cartridge 50 contains fluid reservoir 32 filled with a protein sample and fluid reservoir 34 containing a precipitant solution, as shown in the previous examples. An additional fluid reservoir 80 is located on cartridge 50 which contains a protein and buffer solution. All reservoirs are filled through inlets 52. Fluids from reservoirs 32, 80 flow through microchannels 42 into a channel 82 which operates as an H-Filter to separate unwanted particles into a waste reservoir 84. The filtered solution travels through check valve 38 where it contacts fluid from reservoir 34 to form a laminar flow stream through crystallization chamber 39. Another option is to just filter protein reservoir 32 contents using a 0.22 $\mu$ filter directly incorporated onto cartridge 50 and placed just after the protein fluid reservoir 32 and before check valve 38. This type of filter is typically used to remove particulate matter for dynamic light scattering experiments.

Figure 11:
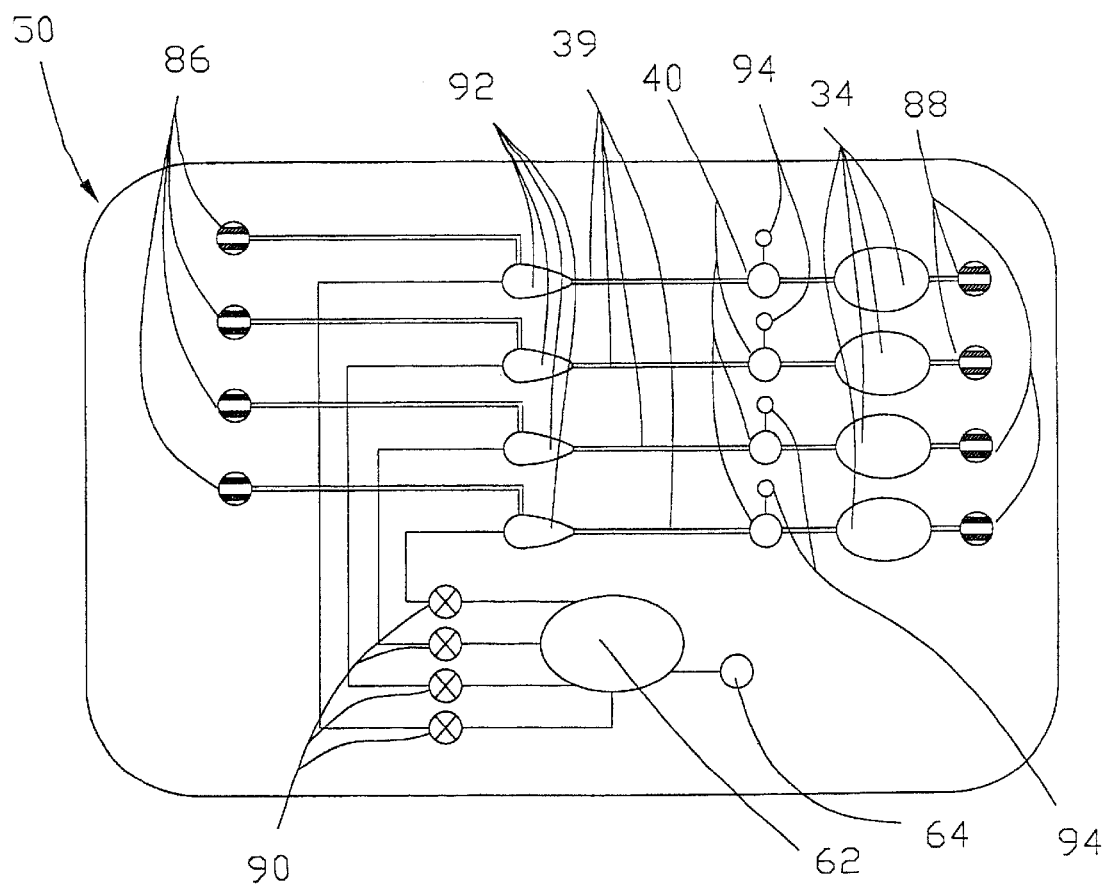
FIG. 11 is a top view showing the loading mode of a microfluidic cartridge for performing high density screening crystallization.

Referring now to FIG. 11, a high density screening crystallization cartridge 50 is shown. Cartridge 50 contains four crystallization chambers 39. Chambers 39 have approximately a 0.5×0.5 mm cross-section. Protein solutions are added at a series of ports 86, while precipitant solutions are added at a series of ports 88. A series of valves 90 couple air bellows 62 to a series of filling chambers 92, which each correspond to a port 86. Each chamber 92 has a capacity of 1–10 $\mu$l. A series of harvesting chambers 40 are each coupled to one of chambers 39. Ports 88 are each connected to a fluid reservoir 34, which in turn are coupled to a corresponding harvesting chamber 40. Each of harvesting chambers 40 has a corresponding vent hole 94. Each harvesting chamber 40 has a capacity of approximately 50 µl, while each fluid reservoir has a capacity of between 0.1 and 0.5 ml.

In operation, ports 86 and 88 are filled with their respective solutions. With valves 90 in the closed position, mixing is achieved as the solutions contact each other within chambers 39 to establish a concentration gradient, as molecules diffuse across the interface zone, thus diluting the protein solution. Valves 90 are then opened individually and the solutions are moved through chambers 39 under the force provided by air bellows 62. During this protein crystallization growth phase, vents 94 and 64, ports 86 and 88, and harvesting chambers 40 are all sealed using adhesive tape. Harvesting occurs by opening valves 90, which forces the contents of crystallization chambers 39 into harvesting chambers 40.

Testing the design of the microfluidic crystallization chips requires the use of protein. Lysozyme and thaumatin PCG systems as initial controls for evaluation of the performance of the chips and instrumentation may be used in this embodiment.

A primary concern is the wetting of the fluid reservoirs to efficiently expel any air bubbles formed during the filling operation. This may be a question of having adequate pipette tips for liquid handling and compatible fluid inlet dimensions. Siliconization may be used to control wetting. Rounded corners, oval or circular fluid reservoir shapes may be examined to minimize bubble entrapment. Dimension and placement of the vent hole should be studied as well as whether filling should be done in a position where the cartridge is slanted to efficiently void air bubbles. All fluids are to be degassed prior to filling.

The shape of the crystallization chamber is important to ensure laminar flow of the two liquids during its filling. A crystallization chamber having a T-sensor structure should be sufficient for operation. However, for rapid inspection of PCG results, it is advantageous to localize PCG in a smaller region. Laminar flow in a crystallization chamber can be readily monitored by injecting two fluids each containing a different colored dye.

The volume of the harvesting chamber should be of sufficient size to allow harvesting of the entire crystallization chamber contents as well as addition of aliquots of mother liquor and cryo-protectant buffer. The harvesting chamber shape should have rounded corners and allow facile access for crystal harvesting.

Plastic clear tape should be used for sealing the fluid reservoirs and harvesting chamber and tested for long-term stability and compatibility with the microfluidic circuit cartridge. Attention should be paid in PCG trials to ease of peeling off the tape from the circuit boards. It may also be advantageous for efficient handling to provide a backing to the plastic clear adhesive tape that peels off exposing the adherent surface for subsequent sealing. Visual cues can be provided on the circuit cartridges of where to place the sealing tape.

The microfluidic cards are made of plastic laminates bonded together with adhesive. The plastic laminate composition is mylar, which is a very resistant material. The fluid compatibility and long-term fluid integrity, however, needs to be assessed and is addressed in the work packages. Problems with PCG fluid compatibility are not anticipated with either the laminate adhesive and mylar. Alternatively, glass or silicon can be used if the fluid incompatibility is severe. Under these circumstances, it should be possible to perform all fluidic development using the laminate method; however, when it comes to mass production, it may be desirable to make the structures out of glass or silicon.

The microfluidic integrated circuit cartridges, when sealed with the covering adhesive film, comprise one level of fluid containment. The fluid driver interface connection on the circuit cartridges is airtight, while the air bellows design does not compromise the containment level. Fifty (50) microfluidic integrated circuit cards containing up to 20 individual PCG experiments each or 1000 PCG experiments in all could fit with external controllers into a sealed container within the volume of a mid-deck locker that provides the second level of containment and, if required, temperature control.

Usually, microfluidic systems require some kind of fluidic driver to operate, e.g., piezoelectric pumps, micro-syringe pumps, electroosmotic pumps, etc. In two previous patent applications, U.S. patent application Ser. No. 09/415,404 and U.S. patent application Ser. No. 60/189,163, which applications are hereby incorporated by reference, there are shown microfluidic systems that are entirely driven by an inherently available force such as gravity, capillary action, absorption in porous materials, chemically induced pressures or vacuums (e.g., by a reaction of water with a drying agent), or by vacuum or pressure generated by simple manual action. Such devices are extremely simple and cheap, do not require electricity, can be manufactured, for example, entirely out of a single material such as plastic, with a method such as injection molding, and are simple to operate.

One embodiment of a device according to the present invention would comprise a hydrostatic pressure-driven cartridge, in which the hydrostatic pressure heads are manufactured as part of the cartridge itself. The cartridge would then be placed on its side so that the gravity pulls the liquids through the channels.

Another embodiment comprises a cartridge on which air spaces under a flexible membrane are in fluid connection with the microfluidic fluid circuit. These compressible airspaces can then be used to aspirate liquids into the channels, or to apply pressure to push liquids to various points on the cartridge, for example, to prime a microfluidic circuit or to siphon fluids until it starts working by gravitational force.

Another embodiment contains chambers in which certain chemical liquids (e.g., ethanol, butane, carbon dioxide, organic solvents, etc. or any substance which has a partial pressure at operating temperature that generates enough force to push liquids through a microfluidic system at desired flow rates) are present in equilibrium with their gaseous phases. These spaces are in fluid connection with parts of the microfluidic circuit and the other reagents, and the pressure in these chambers push the reagents and samples through the channels of the microfluidic circuit.

In addition to filling by gravity or syringe, bellows-driven microfluidic structures have been manufactured in which the bellows are integrated into the laminate as either aspiration or pressurization bubbles. Vents can be placed at various places on the cartridges to allow directional flow of the fluids.

It is also possible to prefill cartridges during manufacturing. A predefined volume of fluid can be placed on a reservoir on an open laminate, which is then sealed with tape, or a cover layer. This action can also be used to drive the fluid to where it should be inside the microfluidic circuit.

While the present invention has been shown and described in terms of a preferred embodiment thereof, it will be understood that this invention is not limited to this particular embodiment and that many changes and modifications may be made without departing from the true spirit and scope of the invention as defined in the appended claims.

What is claimed is:

1. A device for promoting protein crystallization growth from solution, comprising:
   a body structure;
   means located within said body structure for introduction of at least one solution containing protein and at least one solution containing a solvent; and
   at least one microfluidic channel connected to said introduction means wherein said protein solution and said solvent solution interact to induce formation of protein crystals within said channel.

2. The device of claim 1, wherein said protein solution and said solvent solution flow laminarly in parallel contact within said microfluidic channel to establish a concentration gradient within said channel, allowing for protein crystallization.

3. The device of claim 1, wherein said protein solution introduction means and said solvent solution introduction means are each connected to said crystallization channel by a microfluidic channel.

4. The device of claim 3, wherein said protein microfluidic channel, said solvent microfluidic channel, and said crystallization channel form a T-Sensor structure.

5. The device of claim 1, further comprising a chamber coupled to said crystallization channel for harvesting said formed protein crystals.

6. The device of claim 1, further comprising fluid movement generating means coupled to said protein solution introduction means and said solvent solution introduction means for propelling said solutions through said crystallization channel.

7. The device of claim 6, wherein said fluid movement generating means comprises an air bellows.

8. The device of claim 1, further comprising a mixing means, coupled between said protein solution introduction means and said solvent introduction means interface and said crystallization channel for mixing said protein solution and said solvent solution completely to form a homogeneous mixture.

9. The device of claim 8, wherein said mixing means comprises a jet vortex mixer.

10. The device of claim 9, further comprising a solvent absorbing means coupled to said crystallization channel for absorbing solvent from said homogeneous mixture to increase the concentration of protein within said mixture, thereby inducing increased protein crystallization.

11. The device of claim 1, wherein said body structure is constructed from plastic.

12. A device for promoting protein crystallization growth from solution, comprising:
    a body structure;
    means located within said body structure for introduction of at least one solution containing protein, at least one solution containing a solvent, and at least one solution containing a combination of protein and a buffer;
    a microfluidic structure coupled to said protein solvent introduction means and said combination protein and buffer solution introduction means for flowing said solutions laminarly in parallel to remove irreversible protein aggregates from said combined solutions;
    and at least one microfluidic channel connected to said solvent introduction means and the output of said microfluidic structure wherein said solvent solution and said combined solutions interact to induce formation of protein crystals within said channel.

13. The device of claim 12, further comprising a waste chamber coupled to said microfluidic structure to retain said irreversible protein aggregates.

14. The device of claim 12, further comprising a chamber coupled to said crystallization chamber for harvesting said formed protein crystals.

15. The device of claim 12, further comprising fluid movement generating means coupled to said protein solution introduction means, said solvent solution introduction means, and said combined protein and buffer solution introduction means for propelling said solutions through said crystallization channel.

16. The device of claim 15, wherein said fluid movement generating means comprises an air pump.

17. The device of claim 12, wherein said microfluidic structure comprises an H-filter.

* * * * *